United States Patent [19]
Vajtner et al.

[11] Patent Number: 4,963,528
[45] Date of Patent: Oct. 16, 1990

[54] METAL COMPLEXES OF N-METHYL-11-AZA-10-DEOXO-10-DIHYDRO-ERYTHROMYCIN A OR 11-AZA-10-DEOXO-10-DIHYDRO-ERYTHROMYCIN A, METHOD FOR THE MANUFACTURE THEREOF AND THEIR USE IN THE MANUFACTURE OF PHARMACEUTICALS

[75] Inventors: Zlatko Vajtner; Nevenka Lopotar; Slobodan Djoki , all of Zagreb, Yugoslavia

[73] Assignee: Sour Pliva, Yugoslavia

[21] Appl. No.: 94,555

[22] Filed: Sep. 9, 1987

[30] Foreign Application Priority Data

Sep. 12, 1986 [YU] Yugoslavia ............................ 1592/86

[51] Int. Cl.$^5$ .................... A61K 31/71; C07H 17/08
[52] U.S. Cl. ................................ 514/29; 536/7.2; 536/7.4
[58] Field of Search .................... 536/7.2, 7.4; 514/29

[56] References Cited
U.S. PATENT DOCUMENTS 4,328,334  5/1982  Kobrehel et al. ............... 536/7.4
4,474,768  10/1984  Bright .............................. 536/7.4
4,499,083  2/1985  Umezawa et al. .............. 536/16.1

OTHER PUBLICATIONS

Burrows, Textbook of Microbiology (1973), Publ. by W. B. Saunders Company, p. 279.
Niebergall et al., J. Pharm. Pharmac., 1966, 18, 729–738.

Primary Examiner—Johnnie R. Brown
Assistant Examiner—Elli Peselev
Attorney, Agent, or Firm—Pollock, Vande Sande & Priddy

[57] ABSTRACT

New 2:1 complexes of N-methyl-11-aza-10-deoxo-10-dihydroerythromycin A or 11-aza-10-deoxo-10-dihydroerythromycin A with bivalent metals chosen form the group comprising $Cu^{+2}$, $Zn^{+2}$, $Co^{+2}$, $Ni^{+2}$ and $Ca^{+2}$, a process for their manufacture and their use in the manufacture of antibiotically active pharmaceuticals.

New 2:1 complexes of N-methyl-11-aza-10-deoxo-10-dihydroerythromycin A or 11-aza-10-deoxo-10-dihydroerythromycin A with bivalent metals chosen from the group comprising $Cu^{+2}$, $Zn^{+2}$, $Co^{+2}$, $Ni^{+2}$ and $Ca^{+2}$ are made by reacting N-methyl-11-aza-10-deoxo-10-dihydroerythromycin A or 11-aza-10-deoxo-10-dihydroerythromycin A in its free base form or in its water-soluble salt form with salts of said bivalent metals. The compounds possess antibiotic activity.

14 Claims, No Drawings

METAL COMPLEXES OF N-METHYL-11-AZA-10-DEOXO-10-DIHYDROERYTHROMYCIN A OR 11-AZA-10-DEOXO-10-DIHYDRO-ERYTHROMYCIN A, METHOD FOR THE MANUFACTURE THEREOF AND THEIR USE IN THE MANUFACTURE OF PHARMACEUTICALS

The present invention relates to new, biologically active compounds of semisynthetic 15-membered macrolide antibiotics N-methyl-11-aza-10-deoxo-10-dihydroerythromycin A or 11-aza-10-deoxo-10-dihydroerythromycin A with bivalent metals, to methods for the manufacture thereof and to their use in the manufacture of pharmaceuticals.

By means of chemical transformations of the C-9 keto group of erythromycin A there were synthetized 15-membered macrolides possessing a nitrogen atom in the aglycone ring, namely 11-aza-10-deoxo-10-dihydroerythromycin A (U.S. patent 4,328,334) and N-methyl-11-aza-10-deoxo-10-dihydroerythomycin A (Belgian patent No. 892,357 and GB patent No. 2,094,293 resp.), which is an effective antibacterial agent in the treatment of gram-positive and gram-negative microorganisms and exhibited an important activity in preliminary in vivo tests.

It has been known that the presence of metals and the formation of metal complexes resp. might substantially influence the stability, distribution, biotransformation, elimination and other characteristics of pharmaceuticals, especially of antibiotics.

According to the literature (J. Pharm. Pharmac. 18 (1966) 729) erythromycin A may theoretically yield a weak complex with $Co^{+2}$, but it does not yield any complexes with $Cu^{+2}$, $Ca^{+2}$, $Mg^{+2}$, $Ni^{+2}$ and $Zn^{+2}$ ions.

The metal complexes of N-methyl-11-aza-10-deoxo-10-dihydroerythromycin A and 11-aza-10-deoxo-10-dihydroerythromycin A have, according to the Applicant's own search of prior art, not been described as yet.

.. It has now been found that new useful complexes of N-methyl-11-aza-10-deoxo-10-dihydroerythromycin A (Ia) and 11-aza-10-deoxo-10-dihydroerythromycin A (Ib)

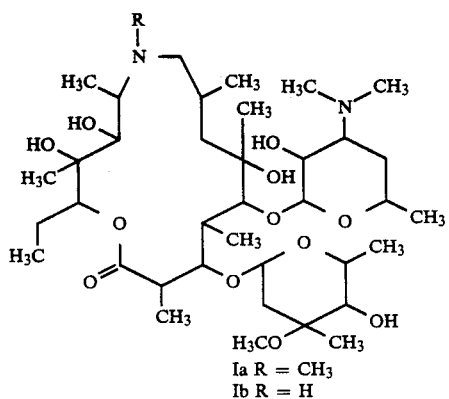

Ia R = CH₃
Ib R = H with bivalent metals chosen from the group comprising $Cu^{+2}$, $Zn^{+2}$, $Co^{+2}$, $Ni^{+2}$ and $Ca^{+2}$ in the ratio of 2:1 may be obtained in a simple manner and in high yields by means of the claimed process.

One object of the present invention are new 2:1 complexes of N-methyl-11-aza-10-deoxo-10-dihydroerythromycin A and 11-aza-10-deoxo-10-dihydroerythromycin A of the above cited formulae Ia and Ib with $Cu^{+2}$, $Zn^{+2}$, $Co^{+2}$, $Ni^{+2}$ and $Ca^{+2}$, which exhibit a superior pharmacological, specifically a superior antibiotic activity.

Another object of the present invention is a new process for the manufacture of said new metal complexes, which is performed in such a manner that N-methyl-11-aza-10-deoxo-10-dihydroerythrmycin A of the formula Ia or 11aza-10-deoxo-10-dihydroerythromycin A of the formula Ib or salts thereof are reacted with salts of bivalent metals chosen from the group comprising $Cu^{+2}$, $Zn^{+2}$, $Co^{+2}$, $Ni^{+2}$ and $Ca^{+2}$, in a molar ratio of 2:1, at ambient temperature.

When the reaction is performed with the compounds Ia or Ib in their salt form, said compounds Ia or Ib are first converted into their water-soluble salts, e.g. a hydrochloride, by means of suitable acids, whereupon the reaction is performed in aqueous solution with a salt of said bivalent metals. The pH of the reaction solution is adjusted to 8–11 by adding alkali lyes (pH-stating) and the product is isolated by means of filtration (method A).

When the reactants Ia and Ib are used in their free base form, the reaction with the metal salt is performed in an alcohol-water mixture while adjusting the pH value by means of alkali lyes and evaporating the alcohol under reduced pressure. The product is isolated by filtration (method B).

The antibiotical activity was assessed on the test organism Sarcina lutea ATCC 9341 as evident from the following Examples. The new complexes exhibited a potent antibiotic activity. Therefore a further object of the present invention is a pharmaceutical composition comprising an effective amount of the new metal complexes of N-methyl-11-aza-10-deoxo-10-dihydroerythromycin A or 11-aza-10-deoxo-10-dihydroerythromycin A, a method of treating human and animal infections, and a method for the manufacture of pharmaceuticals comprising the metal complexes of the compounds of the formula Ia or Ib.

The present invention is illustrated but in no way limited by the following Examples.

Example 1 (Method A)

0.749 g N-methyl-11-aza-10-deoxo-10-dihydroerythromycin A were charged into a 100 ml beaker and dissolved under stirring and the addition of 1 N HCl in 50 ml of water (0.02 M solution) (pH about 6). Then there were added 0.086 g $CuCl_2 \times 2H_2O$ (0.01 M solution with respect to $Cu^{+2}$) and the stirring was continued under a stepwise addition of 0.1 N NaOH until the pH value of 8.5 was achieved. Subsequently, the reaction mixture was stirred for 2 hours at a constant pH value (pH-stating), then the violet colored precipitate was aspirated, washed three times with 10 ml of water and dried; the yield was 0.64 g of the product (81.8 %).

Cu-analysis: (polarographic method, 0.1 N HCl, $E_{\frac{1}{2}} = -0.25$ V;
SCE—saturated calomel electrode)
Calc.: 4.07%
Found: 4.1 %
Activity: 834 U/mg Sarcina lutea ATCC 9341.

Example 2 (Method B)

In 50 ml of a 0.02 M solution of N-methyl-11-aza-10-deoxo-10-dihydroerythromycin A in 60% w/w methanol there were dissolved 0.086 g $CuCl_2 \times 2H_2O$ (0.01 M solution with respect to $Cu^{+2}$). After the adjustment of the pH value to 8.5 with 0.1 N NaOH it was kept stirring for two hours at ambient temperature. The reaction mixture was evaporated at reduced pressure to about half its volume, the violet-colored precipitate was aspirated, washed three times with 10 ml of water, dried and 0.62 g of the product (79.3 %).

The analysis of the product was identical as in Example 1.

Example 3

The process was performed as described in Example 1 with the sole exception that 0.068 g $ZnCl_2$ were added instead of $CuCl_2$ and the pH value was kept adjusted at 8.6. There were obtained 0.61 g of a white-colored product (77.9 %).

Zn-analysis: (atom absorption spectrophotometric method)
Calc.: 4.18%
Found: 4.5%
Activity: 852 U/mg Sarcina lutea ATCC 9341.

Example 4

The process was performed as described in Example 1 with the sole exception that 0.118 g $CoCl_2 \times 6H_2O$ were added instead of $CuCl_2$ and the pH value was kept adjusted at 8.6. There were obtained 0.63 g of a light green-colored product (80.7 %).

Co-analysis: (polarographic method, 0.1 N HCl–0.1 N KCl (1:25),
$E_{\frac{1}{2}} = -1.60$ V; SCE)
Calc.: 3.79%
Found: 4.1%
Activity: 849 U/mg Sarcina lutea ATCC 9341.

Example 5

The process was performed as described in Example 1 with the sole exception that 0.119 g $NiCl_2 \times 6H_2O$ were added instead of $CuCl_2$ and the pH value was kept adjusted at 8.6. There were obtained 0.62 g (79.6 %) of a light green-colored product.

Ni-analysis: (polarographic method, 0.1 N HCl–0.1 N KCl (1:25),
$E_{\frac{1}{2}} = -1,55$ V; SCE)
Calc.: 3.77%
Found: 4.3%
Activity: 852 U/mg Sarcina lutea ATCC 9341.

Example 6

The process was performed as described in Example 1 with the sole exception that 0.074 g $CaCl_2 \times 2H_2O$ were added instead of $CuCl_2$ and the pH value was kept adjusted at 8.6. There were obtained 0.60 g (77.9 %) of a white-colored product.

Ca-analysis: (atom absorption spectrophotometric method)
Calc.: 2.60%
Found: 3.3%
Activity: 856 U/mg Sarcina lutea ATCC 9341.

Example 7

The process was performed as described in Example 1 with the sole exception that 0.735 g 11-aza-10-deoxo-10-dihydroerythromycin A were charged instead of N-methyl-11-aza-10-deoxo-10-dihydroerythromycin A and the pH value was kept adjusted at 9.0. There were isolated 0.62 g of a violet-colored product (80.8 %).

Cu-analysis (polarographic method: 0.1 N HCl)
Calc.: 4.14%
Found: 4.4%
Activity: 495 U/mg Sarcina lutea ATCC 9341.

Example 8

The process was performed as described in Example 2 except that there were charged 0.735 g 11-aza-10-deoxo-10-dihydroerythromycin A instead of N-methyl-11-aza-10-deoxo-10-dihydroerythromycin A and 0.068 g $ZnCl_2$ instead of $CuCl_2$, while keeping the pH value adjusted at 10.0 for three hours. There were isolated 0.53 g (69.0 %) of a white-colored product.

Zn-analysis: (atom absorption spectrophotometric method)
Calc.: 4.10%
Found: 4.6 %
Activity: 530 U/mg Sarcina lutea ATCC 9341.

Example 9

The process was performed as described in Example 4 except that 0.735 g 11-aza-10-deoxo-10-dihydroerythromycin A were charged instead of N-methyl-11-aza-10-deoxo-10-dihydroerythromycin A and the pH value was kept adjusted at 10. There were isolated 0.54 g (70.6%) of a light green-colored product.

Co-Analysis: (polarographic method, 0.1 N HCl–0.1 N KCl)
Calc.: 3.72%
Found: 4.1%
Activity: 435 U/mg Sarcina lutea ATCC 9341.

Example 10

The process was performed as described in Example 9 with the sole exception that 0.118 g $NiCl_2 \times 6H_2O$ were charged instead of $CoCl_2$. There were isolated 0.56 g (73.2%) of a light green-colored product.

Ni-Analysis: (polarographic method, 0.1 N HCl–0.1 N KCl)
Calc.: 3.70%
Found: 4.1%
Activity: 500 U/mg Sarcina lutea ATCC 9341.

Example 11

The process was perfomed as described in Example 9 with the sole exception that 0.074 g $CaCl_2 \times 2H_2O$ were added instead of $CoCl_2$. There were isolated 0.52 g (68.9%) of a white-colored product.

Ca-analysis: (atom absorption spectrophotometric method)
Calc.: 2.55%
Found: 3.0%
Activity: 517 U/mg Sarcina lutea ATCC 9341.

What is claimed is:

1. A complex of N-methyl-11-aza-10-deoxo-10-dihydroerythromycin A of the formula (Ia) or 11-aza-10-deoxo-10-dihydroerythromycin A of the formula (Ib)

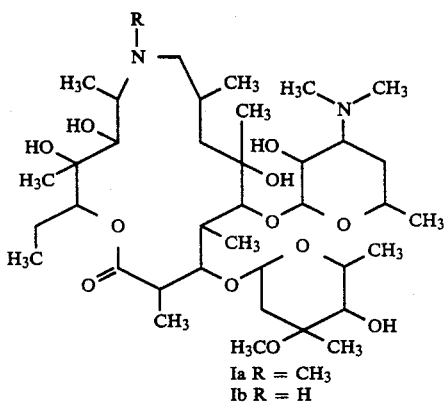

Ia R = CH₃
Ib R = H with bivalent metals chosen from the group consisting of $Cu^{+2}$, $Zn^{+2}$, $Ni^{+2}$, and $Ca^{+2}$ in the ratio of 2:1.

2. The complex of claim 1 wherein said bivalent metal is $Cu^{+2}$.

3. The complex of claim 1 wherein said bivalent metal is $Zn^{+2}$.

4. The complex of claim 1 wherein said bivalent metal is $Ni^{+2}$.

5. The complex of claim 1 wherein said bivalent metal is $Ca^{+2}$.

6. The complex of claim 1 being a complex of N-methyl-11-aza-10-deoxo-10-dihydroerythromycin A (Ia) and a bivalent metal selected from the group of $Cu^{+2}$, $Zn^{+2}$, $Ni^{+2}$, and $Ca^{+2}$ in the ratio of 2:1.

7. The complex of claim 1 being a complex of 11-aza-10-deoxo-10-dihydroerythromycin A (Ib) and a bivalent metal selected from the group of $Cu^{+2}$, $Zn^{+2}$, $Ni^{+2}$, and $Ca^{+2}$ in the ratio of 2:1.

8. A pharmaceutical composition which comprises an antibiotic effective amount of the 2:1 complex of N-methyl-11-aza-10-deoxo-10-dihydroerythromycin A or 11-aza-10-deoxo-10-dihydroerythromycin A with a bivalent metal chosen from the group consisting of $Cu^{+2}$, $Zn^{+2}$, $Ni^{+2}$ and $Ca^{+2}$.

9. A process for preparing a complex of N-methyl-11-aza-10-deoxo-10-dihydroerythromycin A (Ia) or 11-aza-10-deoxo-10-dihydroerythromycin A (Ib)

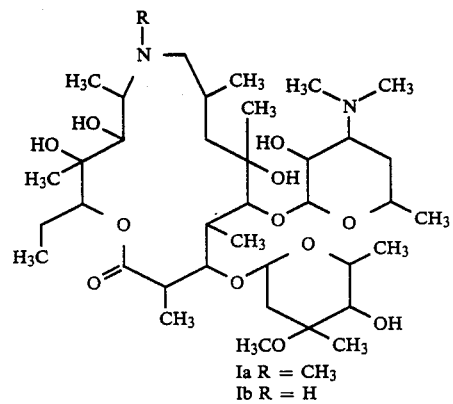

Ia R = CH₃
Ib R = H with bivalent metals chosen from the group consisting of $Cu^{+2}$, $Zn^{+2}$, $Ni^{+2}$ and $Ca^{+2}$ in the ratio of 2:1, which comprises:
the reaction of a compound of the formula (Ia) or (Ib) in the form of its water-soluble salt with a salt of a bivalent metal chosen from the group consisting of $Cu^{+2}$, $Zn^{+2}$, $Co^{+2}$, $Ni^{+2}$ and $Ca^{+2}$, in a molar ratio of 2:1, in an aqueous solution and at ambient temperature while keeping the pH value adjusted at 8-11, and the isolation of the product by means of filtration.

10. A process as claimed in claim 9, wherein the water-soluble salt of the compound (Ia) or (Ib) is a hydrochloride.

11. A process as claimed in claim 9, wherein the metal salt is a chloride.

12. A process as claimed in claim 10, wherein the metal salt is a chloride.

13. A process for preparing a complex of N-methyl-11-aza-10-deoxo-10-dihydroerythromycin A (Ia) or 11-aza-10-deoxo-10-dihydroerythromycin A (Ib)

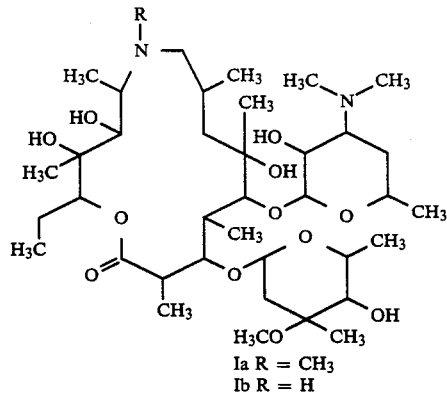

Ia R = CH₃
Ib R = H with bivalent metals chosen from the group consisting of $Cu^{+2}$, $Zn^{+2}$, $Ni^{+2}$ and $Ca^{+2}$ in the ratio of 2:1, which comprises:
the reaction of a compound of the formula (Ia) or (Ib) with a salt of a bivalent metal chosen form the group consisting of $Cu^{+2}$, $Zn^{+2}$, $Ni^{+2}$ and $Ca^{+2}$, in a molar ratio of 2:1, at ambient temperature, in an alcohol-aqueous solution while keeping the pH value adjusted at 8-11 by the addition of alkali lyes, the evaporation of the alcohol under reduced pressure after the performed reaction and the isolation of the product by filtration.

14. The process of claim 13 wherein metal salt is a chloride.

* * * * *